United States Patent
Castellana et al.

[11] Patent Number: 5,250,043
[45] Date of Patent: Oct. 5, 1993

[54] CONTINENT OSTOMATE BANDAGE

[76] Inventors: Frank S. Castellana, 227 Stuart Rd. East, Princeton, N.J. 08540; Keith T. Ferguson, 231 Katherine St., Scotch Plains, N.J. 07076

[21] Appl. No.: 394,703

[22] Filed: Aug. 16, 1989

[51] Int. Cl.[5] ............................................. A61F 5/44
[52] U.S. Cl. ...................................... 604/336; 602/79; 604/337
[58] Field of Search ............... 604/336, 337, 332, 327, 604/378, 307, 304; 128/155, 156; 602/60, 79

[56] References Cited

U.S. PATENT DOCUMENTS

| | | | |
|---|---|---|---|
| 1,845,630 | 2/1929 | Scholl | 128/155 |
| 2,679,248 | 5/1954 | Fullaway . | |
| 2,814,295 | 11/1957 | Hasse . | |
| 2,896,625 | 7/1959 | Austin . | |
| 3,125,093 | 3/1964 | Hutchins . | |
| 3,339,546 | 9/1967 | Chen . | |
| 3,921,629 | 11/1975 | Ekbladh . | |
| 4,085,752 | 4/1978 | Canale . | |
| 4,192,785 | 3/1980 | Chen et al. . | |
| 4,297,995 | 11/1981 | Golub . | |
| 4,393,080 | 7/1983 | Pawalchek et al. . | |
| 4,499,896 | 2/1985 | Heinecke . | |
| 4,551,490 | 11/1985 | Doyle et al. . | |
| 4,706,662 | 11/1987 | Thompson . | |
| 4,762,738 | 8/1988 | Keyes et al. . | |
| 4,786,282 | 11/1988 | Wagle et al. . | |
| 4,787,380 | 11/1988 | Scott . | |
| 4,848,329 | 7/1989 | Dardik . | |
| 4,901,714 | 2/1990 | Jensen | 128/156 |

FOREIGN PATENT DOCUMENTS

| | | |
|---|---|---|
| 0316601 | 5/1989 | European Pat. Off. . |
| 0317058 | 5/1989 | European Pat. Off. . |
| 0317138 | 5/1989 | European Pat. Off. . |
| 778763 | 3/1935 | France .............................. 604/307 |
| 2180756 | 4/1987 | United Kingdom ................ 604/307 |

OTHER PUBLICATIONS

U.S. Patent Application S/N: 242,179 Filed: Nov. 9, 1988 Inventor: Ole R. Jensen Assigned to: E. R. Squibb & Sons, Inc. Now U.S. Pat. No. 4,901,714.

Primary Examiner—Randall L. Green
Assistant Examiner—R. Clarke
Attorney, Agent, or Firm—Richard H. Brink; Stephen B. Davis

[57] ABSTRACT

A bandage including a superabsorbent pad covered by a porous cover pad placed on a thin, flexible hydrocolloid adhesive layer leaving a portion of the adhesive layer around the pads as an adhesive border is disclosed. One side of the adhesive layer is laminated to a polymeric backing or non-woven fabric layer and a protective cover layer is applied over the pads and border portion. The protective cover layer may be silicone coated release paper and the bandage may be subjected to a vacuum thus forming the adhesive layer to the pads resulting in the border portion being substantially coplanar with the exposed surface of the cover pad overlaying the superabsorbent pad.

4 Claims, 3 Drawing Sheets

CONTINENT OSTOMATE BANDAGE

BACKGROUND OF THE INVENTION

The present invention relates to bandages, more particularly, to bandages for applications requiring multiple bandages per day to the same area of the skin.

New surgical procedures today for ostomy care have in some cases eliminated the need for external pouches. A pouch is formed internally by placing a U-bend in the terminal portion of the colon or intestinal track after surgical removal of a portion of the colon. The U-bend ends in a stoma or opening through the abdominal wall in the usual manner but the pouch formed internally by the U-bend is capable of storing a finite amount of discharge. The pouch is emptied four or five times a day by intubation. People who have undergone this type of surgery are often referred to as continent ostomates or ileostomates or urostomates.

The stoma will secrete a certain amount of mucous or discharge which is absorbed by a bandage placed over the stoma. The bandage must be removed and a new bandage applied each time intubation takes place.

A common bandage approach consists of taking a square or rectangular piece of acrylic adhesive, placing a piece of cotton or gauze in the center and placing this over the stoma or, alternatively, taping a piece of cotton or gauze over the stoma. The acrylic adhesive is not particularly friendly to skin upon removal and using this technique four or five times a day often results in skin irritation or even excoriation. A real need exists to provide a bandage for continent ostomates or others such as those suffering with mucous fistulas which bandage will not cause skin irritation, etc. when multiple bandages are used each day to the same area of the skin.

SUMMARY OF THE INVENTION

The present invention is directed to an improved bandage particularly suitable for continent ostomates or others such as those suffering with mucous fistulas. This invention provides a flexible, thin, hydrocolloid adhesive layer having a plastic or non-woven fabric layer affixed to one surface thereof and a superabsorbent pad, smaller than the adhesive layer affixed to the opposite adhesive surface. A porous cover pad covers the superabsorbent pad and leaves a portion of the adhesive layer uncovered to form an adhesive border around the pads.

A protective cover covers the adhesive layer and pads. In one embodiment, the protective cover comprises a plastic cover with a molded cavity having a depth and size to receive the superabsorbent pad and cover pad. Alternatively, the protective cover may be a layer of release paper.

In one embodiment, the hydrocolloid adhesive layer is about eight to twelve mils thick, preferably about ten mils thick, while the plastic or non-woven fabric layer is in the range of 0.5 to 3 mils thick but preferably is a 1 mil thick polyethylene film. The polyethylene layer may be of an opaque color such as flesh colored which may be more aesthetically pleasing and serves to hide blood stains or the like. Also, the polyethylene layer may be embossed.

Preferably, the border portion of the adhesive layer is substantially co-planar with the exposed surface of the cover pad. This can be accomplished by exposing the bandage covered with a layer of release paper to a vacuum. The vacuum removes air from around the pads and when the vacuum is removed the flexible adhesive layer is pressed up against the edges of the superabsorbent pad and the overlaying cover pad.

The invention further provides for placing a narrow strip of release paper along one edge of the adhesive layer before applying the protective cover or layer of release paper which extends over the strip as well.

BRIEF DESCRIPTION OF THE DRAWINGS

FIG. 2A is a cross sectional view of the bandage of FIG. 1 with protective cover and strip of release paper taken along the lines and arrows 2—2 in FIG. 1 before applying the vacuum while FIG. 2B is the same bandage after vacuum forming.

DETAILED DESCRIPTION OF THE DRAWINGS

Figure 1:
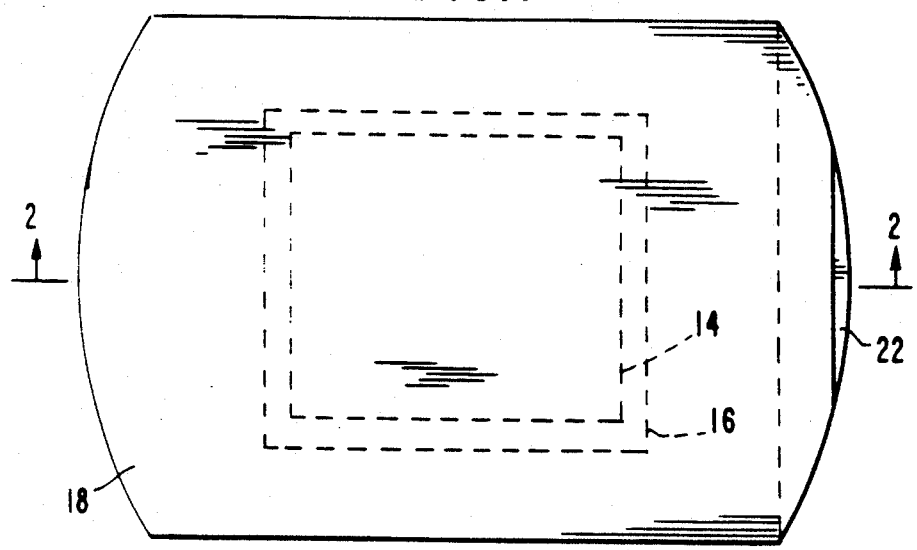
FIG. 1 is a top planar view of the bandage of the present invention.

Referring now to the Figures, a bandage designated generally 10 is shown having an adhesive layer 12, a superabsorbent pad 14, a porous cover pad 16 and a protective cover 18. The adhesive layer 12 is a highly flexible, relatively thin, occlusive hydrocolloid adhesive layer with a backing layer 20 of polymeric material attached to one surface thereof.

To make the bandage as flexible as possible, it is desirable to keep the hydrocolloid layer with backing as thin as possible. A thickness of between 5 mils and 15 mils for the layer 12 is suggested. In the preferred embodiment, a thickness of between 8 and 12 mils is used with 10 mils being most preferable. The polymeric or non-woven fabric layer 20 may be between 0.5 mils to 3 mils. Suitable non-woven fabrics for use as layer 20 include polyester fibers, polypropylene fibers, nylon fibers, composite olefin fibers, and cellulose fibers. Preferably, layer 20 is a polymeric film such as polyethylene with 1 mil embossed polyethylene being most preferred. A suitable polyethylene film is sold under the trade name Tafaflex Code XIX available from Clopay U.S.A. The layer 12 is formed by extruding and is laminated to layer 20. Other polymeric backing films can be selected from the various materials commonly employed in ostomy and medical devices. For example, polyolefins such as polypropylene, ethylene acrylic acids, ethylene vinyl acetates, polyvinylchlorides, polyether sulfones, polyether ketones, polyether urethanes, polyurethanes, etc. can be used.

Unlike prior bandages used by continent ostomates and others requiring like bandages, the preferred adhesive layer 12 of the bandage 10 of this invention is a skin friendly non-acrylic material which is less irritating to the skin. The overall adhesive layer 12 of this invention is flexible and conformable to the body contours of the user and is comfortable for the user.

The adhesive layer 12 is formulated by blending one or more water soluble or swellable hydrocolloids with a polyisobutylene or a mixture of polyisobytylenes or a mixture of polyisobutylenes and other nonacrylic elastomers. Other materials can be included within the adhesive formulations such as mineral oil, tackifiers, antioxidants, cohesive strengthening agents, and pharmaceutically active materials such as antiinflammatory agents, antiseptics, or materials having skin healing or soothing properties. Suitable occlusive adhesive formulations are taught by Chen in U.S. Pat. No. 3,339,546; Chen et al. in U.S. Pat. No. 4,192,785; Pawelchak et al. in U.S. Pat. No. 4,393,080; Doyle et al. in U.S. Pat. No. 4,551,490; and by Keyes et al. in U.S. Pat. No. 4,762,738. As disclosed in these references, suitable water soluble and water swellable hydrocolloids include sodium carboxymethylcellulose, pectin, gelatin, guar gum, locust bean gum, gum karaya, and mixtures thereof. Suitable cohesive strengthening agents include water-insoluable cross-linked sodium carboxymethylcellulose, water-insoluble cross-linked dextran, etc. Suitable non-acrylic elastomers include butyl rubber and styrene radial or block copolymers such as styrene-butadiene-styrene (S-B-S) and styrene-isoprene-styrene (S-I-S) block type copolymers. Preferably, adhesive layer 12 is an adhesive available from the ConraTec division of E.R. Squibb and Sons, Inc. used under the trade name System III adhesive and is a blend on a weight percentage basis of about 19% of a blend of polyisobutylenes (9.5% Vistanex® LM-MH and 9.5% Vistanex® L-100), about 14.5% mineral oil, and about 66.5% of an equal weight mixture of pectin, gelatin, and sodium carboxymethylcellulose.

In one embodiment, porous cover pad 16 is a 1/16 inch thick square or rectangular pad made of cellulose pulp (85 grams per square meter) and polyolefin fibers (22 gsm) and covered by a non-woven cover layer (20 gsm) on its top and bottom. The non-woven cover layer is an air-laid, wet-laid or spun-laid rayon, polyester or prefereably polypropylene. The pad 16 is available in its assembled state from Cellosoft Co. of Sweden and is sold as catalogue #202.150. Alternatively, a pad 16 having a pattern of holes 24 formed through the pad and comprising a combination of polypropylene and tissue can be used. The pad includes a non-woven polypropylene cover on top and bottom and is available from IFC Non Woven, Inc. of Jackson, Florida.

Superabsorbent pad 14 is also about 1/16 inch thick and made substantially the same as the pad 16 availabe from Cellosoft with superabsorbent powder added thereto. A suitable superabsorbent is sold as Salsorb 84 available from Allied Colloid. The superabsorbent comprises about 30% by weight of the pad 14. "Superabsorbents" are water insoluble materials which are capable of absorbing and retaining large amounts of water or other aqueous fluid in comparison to their own weight. Disposable goods manufactured using superabsorbents can be more comfortable, less bulky, and longer lasting than similar products made with traditional absorbents such as cellulose fibers.

Figure 2:
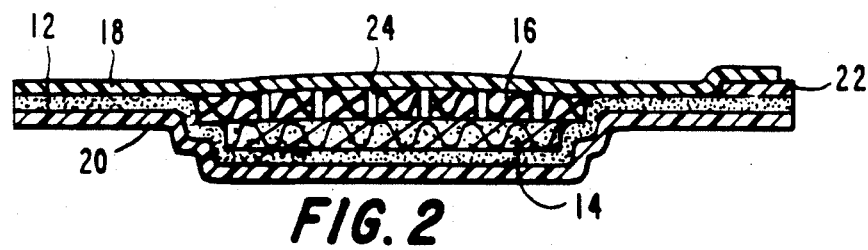
Figure 3:
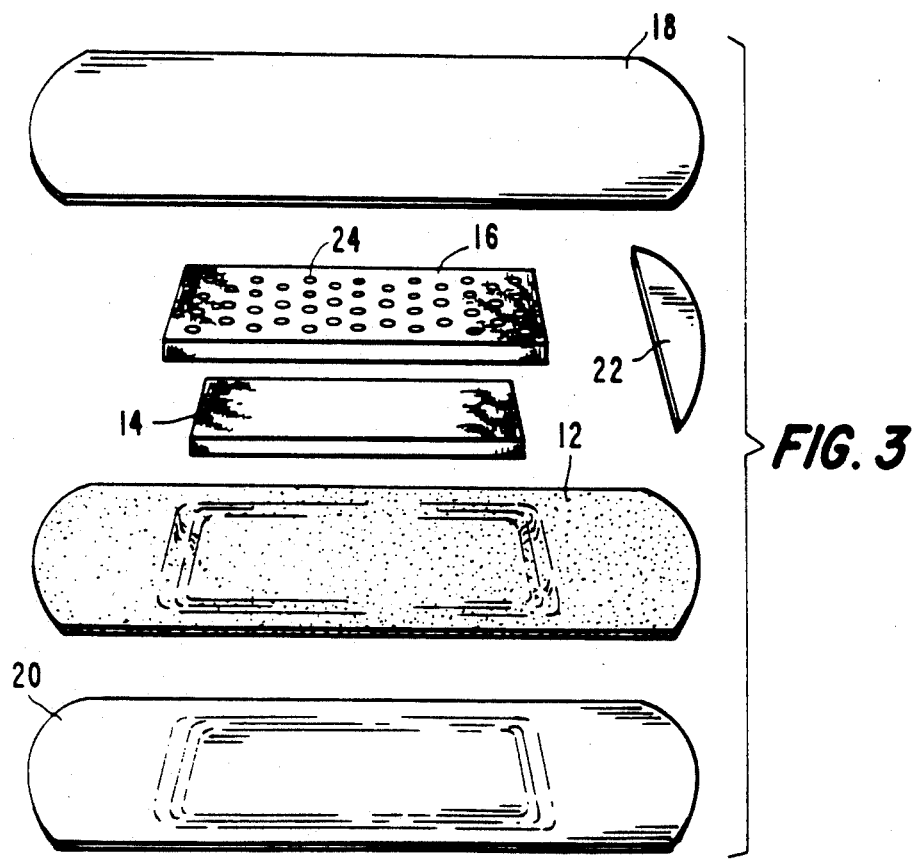
FIG. 3 is an exploded isometric view of the bandage of FIG. 1.
Figure 2A:
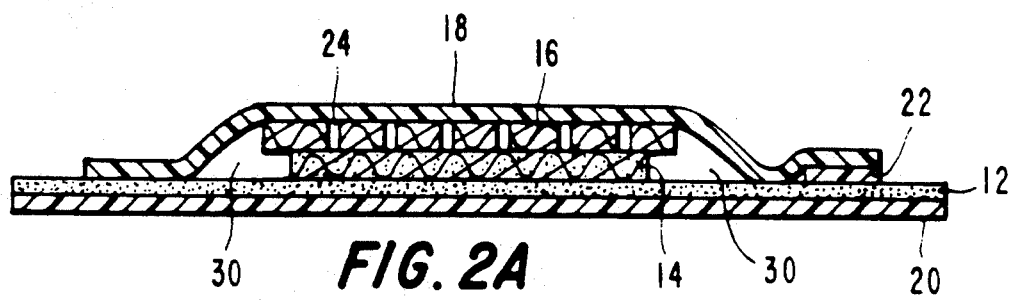

The bandage whose cross-section is depicted in FIGS. 2A and 2B is made by extruding a 10 mil layer of hydrocolloid adhesive and laminating it with a 1 mil embossed polyethylene film on one side and a layer of release paper on the other for handling. The continuous web of combined hydrocolloid adhesive, laminated backing layer and release paper coming from the extruder moves past several work stations to form the bandage. In a continuous fashion the release paper is removed from the adhesive layer 12 to expose an adhesive surface. At a next station, superabsorbent pads 14 are placed on the adhesive layer and covered by cover pads 16. The pads 14 and 16 are pressed down onto the adhesive layer by a platen. Meanwhile, a continuous narrow strip of release paper 22 is applied to one edge of the adhesive surface. A layer of release paper 18 which covers the entire width of the adhesive layer including the pads and release paper strip 22 is applied. Alternatively, a single width of a layer of release paper can be applied over the adhesive. A score line can be applied along one edge of the bandage so that the release paper can be more easily removed. A suitable release paper is a silicone treated paper such as Polysilk S8003 available from HP Smith.

At the next work station, a vacuum is applied to a region surrounding the pads on each side of the web, i.e., to the polyethylene layer on one side and the layer of release paper on the other. The pads are contained within a vacuum chamber along with a border of adhesive with an area of polyetheylene on one side of the adhesive and an area of release paper on top of the exposed border area and the pads. The vacuum removes the air from around the borders of the pads of the bandage trapped between the adhesive layer 12 and the release paper 18. See the regions 30 around pad 14 and pad 16 in FIG. 2A. When the vacuum is removed the adhesive layer 12 which is more flexible than the release paper presses in against the edges of the pads to eliminate most of the region 30. See FIG. 2B. The border region 32 in FIG. 2B of the adhesive layer surrounding the pad 16 is substantially co-planar with the outwardly directed surface 34 of the pad 16 opposite the surface in contact with superabsorbent pad 14. A slight bulge at the center of the pads 14 and 16 may occur. The pads 16 assisted by the pattern of holes 24 conforms quite well to the adhesive layer. At the final work station, bandages are cut from the vacuum formed portions of the web. Preferably, each bandage is rectangular in shape with the smaller sides having curved edges 26 and 28. Two possible sizes are: $4\frac{1}{4}$ inches by 3 inches and 3 inches by $2\frac{3}{8}$ inches. The superabsorbent pad 14 is 2 inches by $1\frac{1}{4}$ inches for the larger size and $1\frac{1}{4}$ inches by 1 inch for the smaller size bandage, while the larger size porous cover pad 16 is $2\frac{1}{4}$ inches by $1\frac{3}{4}$ inches and the smaller size is $1\frac{3}{4}$ inches by $1\frac{1}{4}$ inches. The 1/16 inch thick superabsorbent pads 14 of the size given above are capable of absorbing 10–12 cc's of liquid. Of course, other size bandages and pads are possible.

Figure 4:
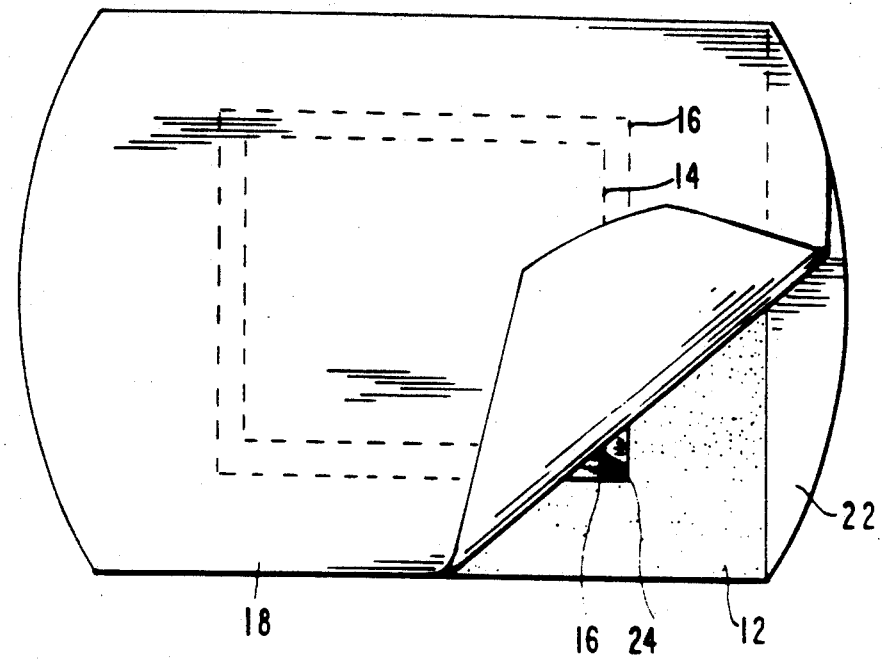
FIG. 4 is a top planar view of the bandage of FIG. 1 with a layer of release paper partially peeled away.

The strip or tab 22 along one side of the bandage facilitates removal of the release paper 18. Since the strip is itself release paper, the strip and layer 18 are easily separated along this edge and then the layer 18 can be stripped away. The strip 22 is useful for holding one edge of the bandage until it is applied and then it is easily removed. FIG. 4 shows the release paper 18 partially peeled away to expose the strip 22. Alternatively, as mentioned before, a single layer of release paper could be applied over the pads and adhesive border area and then scored or partially cut through along one edge to assist in peeling away the release paper.

In use, the release paper layer 18 is peeled away starting at the overlap with strip 22. Then, gripping strip 22, the bandage is applied to the stoma or fistula with the pad 16 next to the stoma. While the pad 16 is somewhat absorbent it is also porous and allows air and fluid to pass through. Pad 16 functions to confine the discharge until it is absorbed by the superabsorbent, keep the superabsorbent from contacting the stoma at the fistula and present a dry surface to the stoma or fistula. The superabsorbent captures and fixes the fluid or discharge. The non-woven layer on the pad 16 next to the stoma or fistula remains dry. Since the fluid is captured by the superabsorbent, the fluid will not travel to the pad 16 from pad 14 even when the bandage is pressed.

Figure 6A:
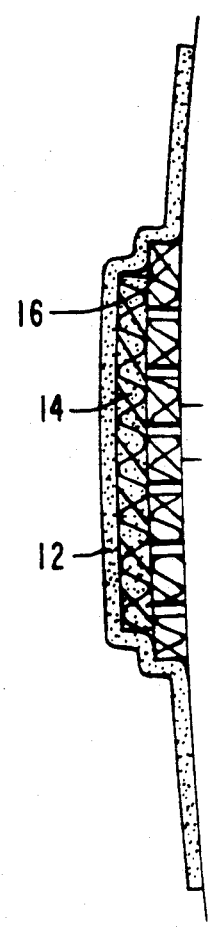
FIGS. 6A and 6B show the bandages of FIG. 2B and 2A, respectively, in cross section applied to the stoma of a user.
Figure 6B:
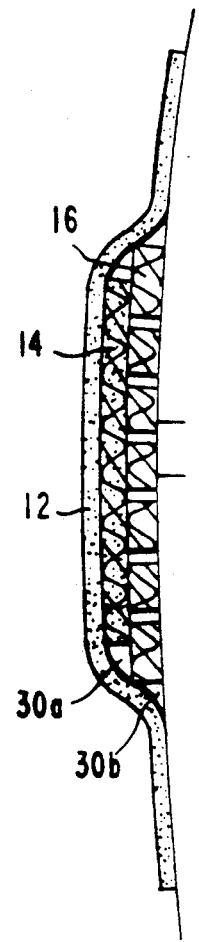

The application of the vacuum to form the adhesive layer 12 to the pads 14 and 16 removes regions where fluid could collect without being absorbed and provides a flat surface for application to the skin and stoma. FIG. 6B shows what would happen if the pad of FIG. 2A were applied to the skin without first vacuum forming the bandage. Region 30 is formed into reservoirs 30a and 30b about the pads where fluid might collect. Using the vacuum formed bandage of FIG. 2B, FIG. 6A shows the reservoirs are reduced.

Figure 5:
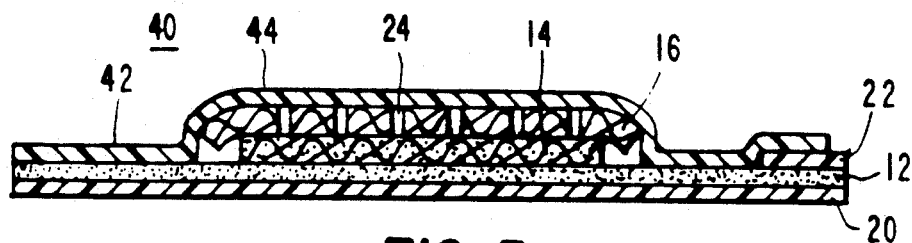
FIG. 5 is a cross sectional view of the bandage of FIG. 2 with an alternate embodiment protective cover taken along the lines and arrows 2—2 in FIG. 1 with no vacuum forming.

An alternate embodiment bandage designated generally 40 is shown in FIG. 5. It comprises the adhesive layer 12 with polymeric backing layer 20, superabsorbent pad 14 with non-woven pad 16. The protective cover 42 is a plastic part with a cavity formed by dish portion 44. The depth and size of the cavity is designed to accept the size and thickness of the pads 14 and 16 where vacuum forming of the bandage is not utilized. The protective cover 42 may be thermoformed polyethylene which is siliconized to make it releaseable from the adhesive border.

The bandage of this invention provides the advantage of a skin friendly adhesive coupled with a superabsorbent pad and a porous cover pad which insulates the stoma from the superabsorbent. The highly flexible and conformable hydrocolloid adhesive is friendly to the periostomal skin upon removal. Multiple bandages can be used each day. The superabsorbent on the other hand absorbs a relatively large quantity of liquid or discharge from the stoma. The bandage thereby forms a substitute for an external ostomy pouch and a good customized design for continent ostomates or others suffering with mucous fistulas.

When the bandage is exposed to a vacuum the adhesive layer is substantially coplanar with the exposed surface of the non-woven pad overlaying the superabsorbent pad. The bandage is easily applied to the stoma forming a low profile bandage when applied.

What is claimed is:

1. A continent ostomate bandage comprising a flexible, hydrocolloid, adhesive layer having a plastic or non-woven fabric layer attached to one side thereof, a superabsorbent pad, smaller in area than said adhesive layer, attached to said adhesive layer on a side thereof opposite from said plastic or non-woven fabric layer, a porous cover pad larger in area than said superabsorbent pad but smaller than said adhesive layer, said porous cover pad overlaying said superabsorbent pad, a portion of said adhesive layer forming an adhesive border around said superabsorbent pad and cover pad and being adapted to adhere the bandage to the skin of said wearer, and a plastic cover overlaying said porous cover pad and attached to said border portion of said adhesive layer, said superabsorbent pad and said porous cover pad together having a predetermined thickness, said plastic cover comprising a molded cavity having a predetermined depth equal to or greater than said thickness and shaped to receive said pads.

2. The bandage of claim 1 wherein said adhesive layer comprises a layer between 5 mils and 15 mils thick and said plastic or non-woven fabric layer comprises a layer between 0.5 mils and 3 mils thick.

3. The bandage of claim 2 wherein said adhesive layer comprises a layer between 8 mils and 12 mils thick and said plastic layer is substantially 1 mil thick.

4. The bandage of claim 1 wherein said adhesive layer comprises a blend on a weight percentage basis of about 19% polyisobutylene, about 14.5% mineral oil, and about 66.5% of an equal weight of pectin, gelatin and sodium carboxymethylcellulose.

* * * * *